(12) United States Patent
Corchs et al.

(10) Patent No.: US 7,349,728 B2
(45) Date of Patent: Mar. 25, 2008

(54) EVALUATION OF IMAGES OF THE BRAIN OBTAINED BY MEANS OF FUNCTIONAL MAGNETIC RESONANCE TOMOGRAPHY

(75) Inventors: Silvia Corchs, Lomazo (IT); Gustavo Deco, Vilassar de Mar (ES); Bernd Schürmann, Haimhausen (DE); Martin Stetter, München (DE); Jan Storck, Germering (DE)

(73) Assignee: Siemens Aktiengesellschaft, Munich (DE)

( * ) Notice: Subject to any disclaimer, the term of this patent is extended or adjusted under 35 U.S.C. 154(b) by 407 days.

(21) Appl. No.: 10/499,619

(22) PCT Filed: Sep. 12, 2002

(86) PCT No.: PCT/DE02/04517

§ 371 (c)(1),
(2), (4) Date: Jan. 21, 2005

(87) PCT Pub. No.: WO03/054794

PCT Pub. Date: Jul. 3, 2003

(65) Prior Publication Data

US 2005/0119558 A1    Jun. 2, 2005

(30) Foreign Application Priority Data

Dec. 20, 2001   (DE) .............................. 101 62 927

(51) Int. Cl.
*A61B 5/055* (2006.01)
(52) U.S. Cl. ..................................... 600/410
(58) Field of Classification Search ................ 600/408, 600/416; 706/15–44
See application file for complete search history.

(56) References Cited

OTHER PUBLICATIONS

Howitz B., Friston KJ, TaylorJG: "Neural modeling and functional brain imaging: an overview", Neural Networks, 2000, 13: S.829-846.

Deco, G.: "Biased competition mechanisms for visual attention", In Emergent Neural Computational Architectures Based on Neuroscience, S. Wermter, J. Austin, and D. Willshaw (Ed.), Springer, Heidelberg, 2001; Online Publication Jul. 24, 2001 S.114-126.

Deco, G. and Zihl, J.: "Top-down selective visual attention: a neurodynamical approach" IN: Visual Cognition, Feb. 2001, 8(1), S. 119-140.

Tagamets M-A and Barry Horwitz "Functional brain imaging and modeling of brain disorders", Progress in Brain Research 1999, Netherlands, Bd. 121, 1999, Seiten 185-200, XP001179681, ISSN: 0079-6123, p. 185-p. 198.

(Continued)

*Primary Examiner*—Eric F. Winakur
*Assistant Examiner*—Michael Rozanski
(74) *Attorney, Agent, or Firm*—Schiff Hardin LLP

(57) ABSTRACT

A method for evaluating an image (fMRI-image) of the brain that has been obtained by functional magnetic resonance tomography is provided. According to the method, a neuronal network is used to simulate the activities of the brain. Supposed disorders of the brain are simulated in the neuronal network (as a disturbed neuronal network). The activities determined in the brain can be artificially simulated in the model and its effect on the complex synergy of the areas of the brain can be quantified. The comparison with the fMRI image or fMRI activity pattern relating to the patient enables the cause of the disorders to be localized, thus leading to a successful diagnosis.

12 Claims, 2 Drawing Sheets

OTHER PUBLICATIONS

Arbib M.A., A. Billard, M. Iacoboni, E. Oztop: "Synthetic brain imaging: grasping, mirror neurons and imitation", Neural Networks 13 (2000) 975-997 2000 Special Issue, Published by Elsevier Science LTD., Publishers, Barking, GB, Bd. 13, Nr. 8-9, XP004226357, ISSN: 0893-6080.

NR Taylor & JG Taylor "Modelling the Frontal Lobes in Health and Disease" Proceedings of 9th International Conference on Artificial Neural Networks: ICANN '99, Edinburgh, UK, Sep. 7-10, 1999, pp. 401-406, vol. 1, XP002272131.

B. Horwitz, K.J. Friston, J.G. Taylor: "Neural modeling and functional brain imaging: an overview" Neural Networks, Elsevier Science, Publishers, Barking, GB, Bd. 13, Nr. 8-9, Nov. 2000, pp. 829-846, XP004226347.

Gustavo Deco, Bernd Schürmann, "A hierachical neural system with attentional top—down enhancement of the spatial resolution for object recognition", Vision Research, Pergamon Press, Oxford, GB, Bd. 40, Nr. 20, 2000, pp. 2845-2859, XP000952194.

O.Monchi, J.G. Taylor, A. Dagher A neural model of working memory process in normal subjects, Parkinson's disease and schizophrenia for fMRI design and predictions; 2000 Elsevier Science Ltd., pp. 953-973.

Peter T. Fox and Marcus E. Raichle "Focal physiological uncoupling of cerebral blood flow and oxidative metabolism during somatosensory stimulation in human subject"; Proc. Natl. Acad. Sci. USA, vol. 83, pp. 1140-1144, Feb. 1986.

Gustavo Deco, Dragan Obradovic "An Information-Theoretic Approach to Neural Computing"; ISBN 0-387-94666-7 Springer-Verlag, New York Berlin Heidelberg SPIN 10524292, Chapter 5; and pp. 126-133.

Sabine Kastner, Mark A. Pinsk, Peter De Weerd, Robert Desimone and Leslie G. Ungerielder, "Increased Activity in Human Visual Cortex during Directed Attention in the Absence of Visual Stimulation"; Laboratory of Brain and Cognition; Neuron, vol. 22, pp. 751-761, Apr. 1999.

Sabine Kastner, Peter De Weerd, Robert Desimone and Leslie G. Ungerielder, "Mechanisms of Directed Attention in the Human Extrastriate Cortex as Revealed by Functional MRI"; Science vol. 282, Oct. 2, 1998, pp. 108-111.

Marius Usher and Ernst Niebur "Modeling the Temporal Dynamics of IT Neurons in Visual Search: A Mechanism for Top-Down Selective Attention"; Journal of Cognitive Neuroscience, 1996 Massachusetts Institute of Technology; 8:4, pp. 311-327.

Seiji Ogawa, Tso-Ming Lee, Asha S. Nayak and Paul Glynn "Oxygenation-Sensitive Contrast in Magnetic Resonance Image of Rodent Brain at High Magnetic Fields"; Magnetic Resonance in Medicine 14, pp. 68-78 (1990).

EVALUATION OF IMAGES OF THE BRAIN OBTAINED BY MEANS OF FUNCTIONAL MAGNETIC RESONANCE TOMOGRAPHY

BACKGROUND OF THE INVENTION

1. Field of the Invention

The present invention relates generally to a method and apparatus for evaluating brain images obtained by functional magnetic resonance imaging and in particular to simulation of brain activity using neuronal network.

2. Description of the Related Art

Thanks to rapid developments in the area of functional Magnetic Resonance Imaging, fMRI for short, or functional Magnetic Resonance Tomography, fMRT for short, increasing success has been achieved in recording the distribution of brain activity of patients during the resolution of complex perception and planning tasks and of motor tasks.

The enormous possibilities of this technology are still however at odds with their current benefits for investigation and diagnosis in neurology and neurosurgery.

The main reason for this discrepancy lies in the complexity of the brain. The human brain cortex alone can be divided up into around 200 functional units, the brain areas, between which there are around 10,000 backwards coupled, dense networking paths. The networking paths each consist of a number of synaptic connections, that is nerve bundles.

As a result of this complex structure as well as the distributed parallel signal processing in the brain, malfunctions can only very rarely by read off clearly from the change of activity in the fMRI image—in a area—for example. Disturbances to the cerebral functions manifest themselves as a rule rather as a change, compared to healthy people, in the interaction between the areas, which in its turn modifies the activity status of the entire brain in a complex manner.

This presents the doctor with the extremely serious and thus far, except for a few special cases, unresolved problem of determining from the measured complex striking features in the fMRI image the actual cause of the cerebral disturbance.

SUMMARY

The present invention increases the usefulness of fMRI images for diagnosis. This is achieved by a method for evaluating an image of the brain (fMRI image) obtained by functional magnetic resonance tomography, in which, a neuronal network is used to simulate the activities of the brain; a disturbance suspected in the brain is simulated in the neuronal network (as a disturbed neuronal network); the activity determined in the disturbed neuronal network is compared with the activity of the brain observed in the fMRI image; and from the comparison conclusions are drawn about disturbances in the brain.

The present invention also relates to an arrangement for evaluating an image of the brain (fMRI image) obtained by means functional magnetic resonance tomography, having with a neuronal network used to simulate the activity of the brain; with means for simulating a suspected disturbance in the brain in the neuronal network (disturbed neuronal network); with means for comparison of the activity determined in the disturbed neuronal network with the activity of the brain observed in the fMRI image; and with means for excluding disturbances in the brain from the comparison.

BRIEF DESCRIPTION OF THE DRAWINGS

The invention is explained in more detail below using examples which are shown in the figures. The same reference numbers in individual figures identify the same elements in each case.

DETAILED DESCRIPTION OF THE PREFERRED EMBODIMENT

Figure 1:
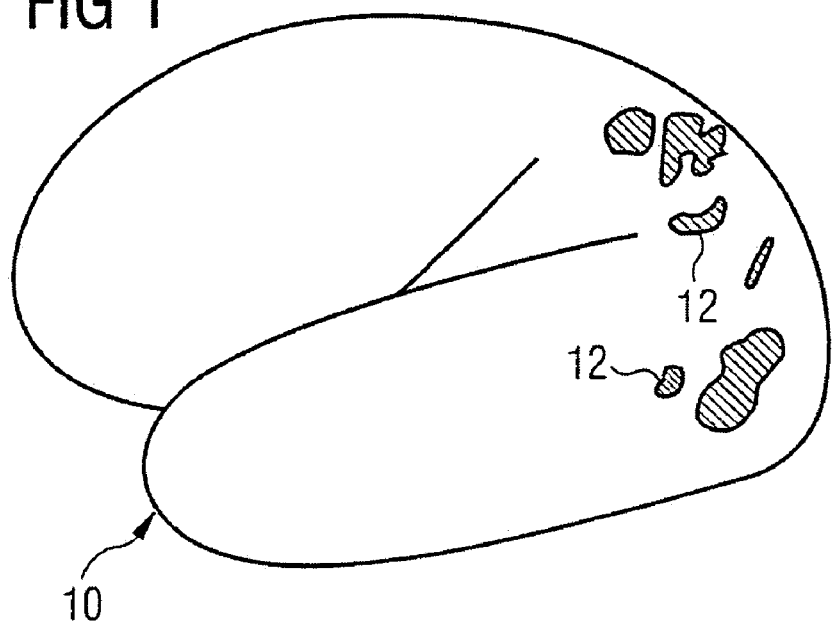
FIG. 1 is a schematic representation of a brain scan showing an example of an fMRI image.

In accordance with the invention, a method for evaluating an image (fMRI image) of the brain obtained by functional magnetic resonance tomography is provided. A neuronal network is used to simulate the activities of the brain. Suspected disturbances in the brain are simulated in the neuronal network (simulated neuronal network). The activities determined in the disturbed neuronal network are compared to the activities observed in the fMRI image. The comparison leads to conclusions being drawn about disturbances in the brain.

The possible cause of the disturbances can be subdivided into number of classes:

(a) Failures or partial failures in one area.

(b) Complete failure of one of more connection paths between two or more areas.

(c) Failures at the cellular level which for example result in a changed short-term dynamic of the nerve populations, e.g. within an area.

Only the first class (a) of disturbance causes can be made out directly in the fMRI image. The effects of these disturbances on the other areas are however complex because of the dense network and demand quantification.

The other two classes of disturbance causes, (b) and (c), can have very hidden effects. For example it follows from the dense networking of the brain areas that the complete interruption of the connection between two areas has effects not only on the two areas involved. An interruption of the connection changes the overall signal propagation through the brain and thus causes indirect disturbances to other brain functions that are seemingly unconnected with the areas observed.

In accordance with the invention, a doctor is provided with a tool with the aid of which the complex interaction of a number of brain areas can be simulated during the resolution of defined tasks by the brain. The simulator is based on simulating the dynamics of coupled populations of neurons, that is on a neuronal network. The dynamic simulation simulates the time sequence of the activities of the neurons.

The failure of any substructure in the brain can be artificially simulated in the model and its effect on the complex interaction of the areas of the brain can be quantified. The comparison with the fMRI image or activity pattern taken for the patient results in the localization of the cause of the disturbance and thereby in successful diagnosis. A quantitative relationship is thus established between the measured spatial distribution of the brain activity on the one side and the medically relevant brain status on the other side.

As well as its simulation of the brain on the basis of the multiplicity of individual neurons, the neuronal network can also feature a structure which is similar to the structure of the brain in its division into areas and their connections. This leads on one hand to a reduction of the complexity of the neuronal network. On the other hand the neuronal network corresponds in its structures to the structures of the brain.

Advantageously a third-generation neurosimulator (neurocognition) is thus used for quantitive interpretation and thereby investigation of fMRI images. Models of networks of neurones on a more or less static basis are called first-generation neurosimulators, they are the classical neuronal networks models of the dynamic behavior of the neurons, especially the pulses generated within them are called second-generation neurosimulators. Finally models of the organization at the neurons into pools and the pools into areas are called third-generation neurosimulators. In this case a pool comprises thousands of neurons.

The method in accordance with the invention can be integrated as an analysis tool into the operating software of a computer which controls an fMRI tomograph, or can operate as a self-contained diagnosis support device.

The advantages of the invention are achieved by a computer program that, when run on a computer executes the method in accordance with the invention as well as by a computer program with program code means in order to execute all steps in accordance with the invention when the program is executed on a computer.

The advantages are also achieved by a computer program with a program code which is stored on a computer-readable data medium. The invention also provides a computer program product with program code stored on a machine-readable medium to execute all steps in accordance with the invention when the program is executed on a computer. Finally, the invention provides a data medium on which a data structure is stored which after being loaded into the main memory of a computer, executes the method in accordance with the invention.

The method of operation of neurocognitive modeling is described below using visual attention phenomena.

Initially fMRI images of the distribution of activity in the brain must be recorded With Positron-Emission Tomography (PET), a method which can show material changes and changes in blood flow in the brain with the aid of radioactively-marked substances. Using these radioactively-marked substances, it could be shown that activating particular areas of the brain leads to a local increase in blood flow and in use of oxygen by the nerve cells (Fox PT, Raichle Me: "Focal physiological uncoupling of cerebral blood flow and oxydative metabolism during somatosensory stimulation in human subjects" Proceedings of the National Academy of Science of the USA, 1986, Volume 83, Pages 1140-1144). The delivery of oxygen-rich, arterial blood required for this is thus increased locally. Normally the blood flow however increases disproportionately to the consumption of oxygen so that the result is a superfluity of oxygenated hemoglobin in the venous outflow area.

Functional Magnetic Resonance Tomography (fMRT) uses the fact that the oxygen content of the blood influences its magnetic properties and thus leads to a different signal generation in the magnetic resonance tomography. Since the magnetic characteristics and thus the signal generation of the blood change with the contents of oxygenated or deoxygenated hemoglobin, blood behaves in functional Magnetic Resonance Tomography like an (endogenous) contrast medium Which a high proportion of deoxygenated hemoglobin, as a result of its paramagnetic characteristics in the environment of the vessels, a local magnetic field gradient is induced which, with a suitable choice of MRT measuring sequence (e.g. gradiant echo sequence or corresponding echo planar imaging) frequently leads to a local signal reduction. If the proportion of oxygenated hemoglobin in the blood increases, what is known as the susceptibility effect decreases. This leads to an increase in the measurement signal. This relationship is referred to as the BOLD (blood oxygen level dependent contrast) With increasing the field strength of the magnetic resonance tomographs this effect increases [Ogawa S, Lee TM, Nayak AS, Glynn P: "Oxygenation-sensitive contrast in magnetic resonance image of rodent brain at high magnetic fields." Magnetic Resonance Medicine, 1990, Volume 14, Pages 68-78], so that devices with a magnetic field strength of 1.5 Tesla and greater are used for functional MRT (fMRT).

The local changes of the oxygen content in the blood during activation processes can be presented by means of fMRI with high spatial resolution and exactly assigned to the individual anatomical structures of the brain.

fMRI can thus be used to determine which areas of the brain are active at a given point in time or during an activity and which are not, or to what extent individual brain areas are active.

A schematic example of an fMRI recording can be seen in FIG. 1. FIG. 1 shows a view of the left half of the brain 10 with brain lobes indicated. The Figure shows an image of a patient who was presented with the task of finding a point in a picture. To solve this problem the brain areas 12 shown cross-hatched are activated, which can be seen on the fMRI image.

The aim of the modeling is a more detailed neuronal network model of the areas of the brain which reflects the real circumstances in the brain for activation processes, especially as regards the visual attention control and thereby an explanation of these functions by physiological mechanisms.

With classical image processing models, such as digital image processing, a recorded image is analyzed by means of a so-called bottom-up approach in successively higher levels of processing.

By contrast to these classical models of image processing it has been shown that what is known as a top-down approach better reflects the real circumstances of the visual cortex. With the top-down approach intermediate results are used at a higher level by means of feedback to once again usefully evaluate lower processing levels. The important factor is the moment of feedback between the individual levels. In the model to be shown in concrete terms further on this feedback is implemented by the interaction of the individual areas.

The feedback leads to a shift in the equilibrium in the attention competition of the individual neurons or groups of neurons. The result is thus an unequal competition for the attention ("biased competition"). Only an increased attention for a specific spatial area or a feature and an associated neglect of the other features or spatial areas allows a reduction of the volume of data of an image and thus specific perception of individual objects.

In the search for a feature in an image, for example the Eiffel Tower of Paris, a decision would be made between two questions in classical image processing:
   The first question is: Where is the Eiffel Tower? This is what is known as a "where" question. It searches for the location of the known feature in the image (a search).
   The second question is: Which object is to be seen in the middle of the picture? This is a so-called "what"-question, the question about recognizing an object from a given location (an object detection).

The "where" question is classically answered by searching the entire image with the aid of a specified attention window. The "what" question is answered by comparing the known pattern with the specified image section or by searching at the specified image section for features on to which the attention is concentrated in order to detect the image characteristics.

With the new top-down approach the entire image is processed in parallel. The features searched for emerge during processing, i.e. they become prominent after a while by the fact that those "grandmother pools" (see below) become active which have won the competition between the individual pools or features. The "what"- and the "where" question are answered with the same model. Merely the input bias (see below) is changed, i.e. the attention is shifted in the direction of what or where. An attitude of expectation is created by means of the bias.

For modeling this top-down approach, what is known as a third generation neurosimulator is used. Third-generation neurosimulators are identified as those hierarchical models of the organization of the neurons into pools and the pools into areas, corresponding to areas of the brain as is described below using the visual cortex as an example. In this case a pool comprises thousands of neurons.

Figure 2:
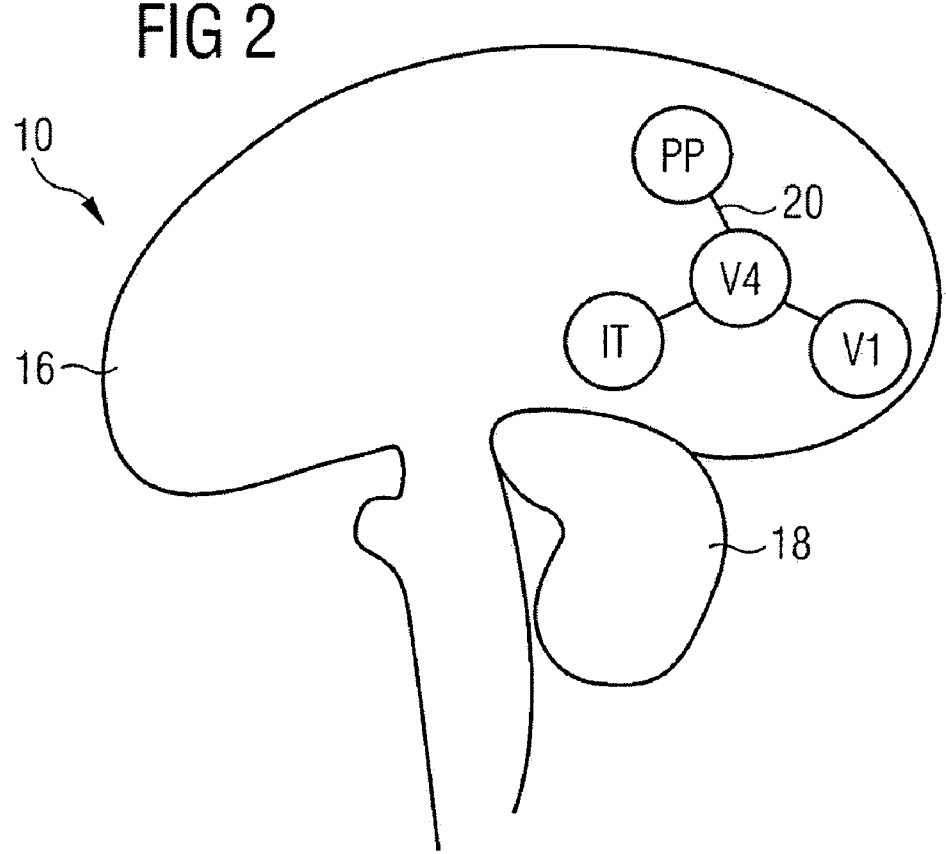
FIG. 2 is a simplified diagram of the major areas of the visual cortex of the brain.

FIG. 2 shows a simplified diagram of the main areas of the visual cortex of the brain 10. The cerebrum 16 and the cerebellum 18 are mapped. In the cerebrum 16 the visual cortex contains among others the areas shown and explained in more detail below V1, V4, PP and IT. Between these areas there are many-stranded synaptic connections 20.

Figure 3:
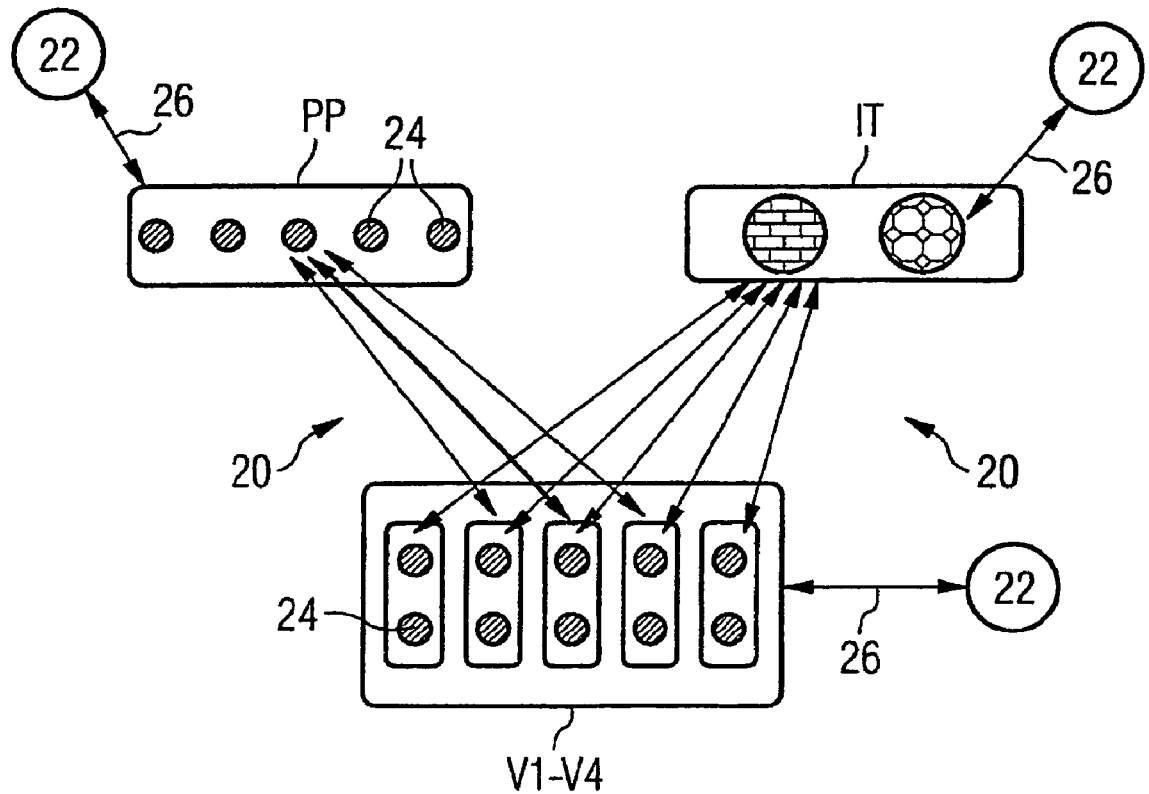
FIG. 3 is a abstract reproduction of the areas of the brain and their synaptic connections.

The structure of the mathematical model will now be described in detail with reference to FIG. 3 which represents an abstract reproduction of the circumstances in the brain.

The IT (inferotemporal) area is used for image recognition or object recognition within an image ("what" question). In it are stored image patterns which can correspond to the representations of objects of the visible world. Two typical patterns are shown, bricks or webs. A pattern is recognized if a maximum of one so-called "grandmother neuron" assigned to the pattern becomes active. The capability of the "grandmother neuron" to detect a specific pattern is acquired by training. The present model does not operate with "grandmother neurons" to detect patterns but with the smallest unit of the model: the pool. A pattern is thus detected by a "grandmother pool" if the corresponding grandmother pool is active to the maximum. Accordingly the IT area in the present model contains just as many pools as there are patterns or objects to be detected.

The PP (posterior parietal) area is used for localizing known patterns ("where" question). The area PP thus contains in the present model as many pools 24 as there are pixels in the image to be recognized. The concentration of neuronal activities into a small number of adjacent pools in PP corresponds to localization of the object.

The areas V1 and V4 are combined in the present model into the area V1-V4 which is also designated V4. This area is generally responsible for the extraction of features. It contains around 1 million pools 24, a pool for each feature. The pools 24 address individual features of the image. The features of the image are produced from a Wavelet transformation of the image (see below). A feature in this case is defined by a specific size or spatial frequency, a spatial orientation and a specific location in the x and y direction (see below). All recorded image data first reaches the area V1-V4.

In addition for each area there is at least one inhibitory pool 22, that is a pool which exercises an inhibitory effect on the activities of other pools. The inhibitory pools are linked by bidirectional connections 26 to the excitable pools 24. The inhibitory pools 22 produce competitive interaction or competition between the pools. The competition in V1-V4 is undertaken with pools 24 which encode both location and object information. The PP abstracts location information and transfers a competition to the spatial level. IT abstracts information from classes of objects and communicates a competition at the levels of the classes of objects.

Between the areas there are synaptic connections 20, through which the pools 24 can be excited into activity. The area IT is linked to the area V4. The area PP is linked to the area V4. The synaptic connections 20 between the areas simulated in the model reflect the "what"- and the "where" path of visual processing. The "what" path connects the area V4 with the area IT for object recognition. The "where" path connects the area V4 with the area PP for localization. The areas IT and PP are not connected to each other.

The synaptic connections 20 are always bidirectional, i.e. the data from V4 is further processed in the PP or IT. At the same time the results from PP or IT are also fed back into V4, to control the competition for the attention.

The activities of the neuronal pools are modeled using the mean field approximation. Many areas of the brain organize groups of neurons with similar characteristics into columns with field combinations, such as for example orientation columns in the primary visual cortex and in the somatosensory cortex. This group of neurons, the pools, are made up of a large and homogeneous population of neurons which receive a similar external input, are linked to each other and probably function together as a unit. These pools can form a more robust processing and encoding unit since their instantaneous population average value response, by contrast to the timing means of a relatively stochastic neuron in a large time window is better adapted to the analysis of fast changes in the real world.

The activity of the pools of neurons is described with the aid of the mean field approximation. In this case the pulse activity of a pool is expressed by an ensemble average value x of the pulse rate of all neurons of the pool. This average activity x of the pool is produced by excitation of the neurons of the pool by an input pulse stream I:

$$x(t)=F(I(t)). \qquad (1)$$

Here F is a real function. For pulsed neurons of type "integrate and fire" which react deterministically to the input current I, in an adiabatic approximation (Usher, M. and Niebur, E.: "Modeling the temporary dynamics of IT neurons in visual search: A mechanism of top-down selective attention", Journal of Cognitive Neuroscience, Pages 311-327 (1996)):

$$F(I(t)) = \frac{1}{T_{refractory} - \tau \log\left(1 - \frac{1}{\tau I(t)}\right)}, \qquad (2)$$

where $T_{refractory}$ specifies the dead time of a neuron after the sending out of a pulse (around 1 ms) and $\tau$ the latency of the membrane of the neuron, that is the time a between an external input and the complete polarization of the membrane (Usher, M. and Niebur, E.: "Modeling the temporary dynamics of IT neurons in visual search: A mechanism of top-down selective attention", Journal of Cognitive Neuroscience, Pages 311-327 (1996)). A typical value for $\tau$ is 7 ms.

The activity of anisolated pool of neurons can also be characterized by the average activity x also by the strength of the input current I flowing between the neurons. This develops over time in accordance with the following equation:

$$\tau \frac{\partial}{\partial t} I(t) = -I(t) + \tilde{q} F(I(t)) \qquad (3)$$

Here the first term on the right hand side describes the decay of the activities and the second term on the right hand side the self—excitation between the neurons within the pool. The second term describes the co-operative excitation interaction in the pool. $\tilde{q}$ parameterizes the strength of the self-excitation A typical value for $\tilde{q}$ is 0.8.

The images taken directly are to be encoded in a grey scale image which is described through an n×n matrix $$\Gamma_{ij}^{orig}.$$

A non-quadratic matrix is also possible. Normally operation is with a 64×64 matrix, i.e. n=64. In this case the indices i and j designate the spatial position of the pixels. The grey scale value $$\Gamma_{ij}^{orig}$$

within each pixel is preferably encoded by 8 bits. In this case the bit value 0 corresponds to the value of black and the bit value 255 to the color white.

In the first processing step the constant component of the image is subtracted. This is done in the brain presumably by the LGN (lateral geniculate nucleus) of the Thalamus. The n×n image matrix is obtained by subtracting the average value $\Gamma_{ij}$:

$$\Gamma_{ij} = \Gamma_{ij}^{orig} - \frac{1}{n^2} \sum_{i=1}^{n} \sum_{j=1}^{n} \Gamma_{ij}^{orig}. \qquad (4)$$

The extraction of features from the image by the pools in area V4 occurs in accordance with the model in the way in which the pools execute a Gabor-Wavelet transformation of the image, more precisely that the activity of the pools corresponds to the coefficients of a Gabor-Wavelet transformation.

The functions used for the Gabor-Wavelet transformation $G_{kqpl}$ are functions of the location x and y are all the discreet indices i and j and are defined by $$G_{kpql}(x,y) = \alpha^{-k} \Psi_{\theta_l}(\alpha^{-k}(x-2p), \alpha^{-k}(y-2q)), \qquad (5)$$

where $$\Psi_{\theta_l}(x,y) = \psi(x \cos(l\theta_0) + y \sin(l\theta_0), -x \sin(l\theta_0) + y \cos(l\theta_0)). \qquad (6)$$

The basic wavelet $\psi(x, y)$ is defined by the product of an elliptical Gauss function and of a complex smooth wave:

$$\psi(x, y) = \frac{e^{-\frac{1}{8}(4x^2 + y^2)}}{\sqrt{2\pi}} \left[ e^{ikx} - e^{-\frac{k^2}{2}} \right]. \qquad (7)$$

The Gabor-Wavelet functions thus possess four degrees of freedom k, l, p and q.

k corresponds to the size of the feature, expressed by the octave k, that is the spatial frequency, determined through the 2^kth of the basic frequency, which is scaled through the parameter a; the value 2 is generally selected for a.

l corresponds to the angle orientation expressed by $\theta_l = l \cdot \theta_0$. $\theta_l$ is thus a multiple of the angle increment $\theta_0 = \pi/L$, that is the orientation resolution. Values of between 2 and 10 are preferably chosen for L.

p and q determine the spatial location of the midpoint c of the function in the x and y direction, expressed by $$c = (c_x, c_y) = (2p, 2q) \qquad (8)$$

Consequently the activity $$I_{kpql}^{V4}$$

of a pool in the area V4 which accesses the spatial frequency or the octave k, the spatial orientation with the index i and an event for which the center is determined by p and q, is excited by $$I_{kpql}^{V4,E}$$

with $$I_{kpql}^{V4,E} := \sqrt{\|\langle G_{kpql}, \Gamma \rangle\|^2} := \sqrt{\left\| \sum_{i=1}^{n} \sum_{j=1}^{n} G_{kpql}(i,j) \Gamma_{ij} \right\|^2}. \qquad (9)$$

In accordance with the model this precisely corresponds to the coefficients of the Gabor-Wavelet transformation. The relevant behavior of the pool is defined by way of a prior training (see below).

We will now look at the neurodynamic equations which govern the timing development of the system.

The activity $$I_{kpql}^{V4}$$

of a pool in the area V4 with features which are described by the parameters k, p, q and l described above, is developed in the continuation of the equation (3) by the inhibitory and excitation input streams in the time in accordance with $$\tau \frac{\partial}{\partial t} I_{kpql}^{V4} = \qquad (10)$$

-continued
$$-I_{kpql}^{V4} + \tilde{q}F(I_{kpql}^{V4}) - bF(I_k^{V4,l}) + I_{kpql}^{V4,E} + I_{pq}^{V4,PP} + I_{kpql}^{V4-IT} + I_0 + v.$$

The first two terms on the right hand side are explained earlier on this document. They represent the natural decaying of the activities or the self-excitation within the pool.

The third term on the right hand side of the equation (10), $$bF(I_k^{V4,l}),$$

describes the above-mentioned inhibitory effect of the inhibitory pool 22 which is described in more detail further on. The parameter b on the right hand side of the equation (10) scales the strength of the inhibition. A typical value for b is 0.8.

The fourth term on the right hand side of equation (10), $$I_{kpql}^{V4,E},$$

describes the excitation by the recorded image in accordance with the Gabor-Wavelet transformation as per equation (9).

The fifth term on the right hand side of equation (10), $$I_{pq}^{V4-PP},$$

describes the attention control for a feature with the spatial location corresponding to p and q, that is for stressing the "where" question, as is explained further on in this document.

The sixth term on the right hand side of equation (10), $$I_{kpql}^{V4-IT},$$

describes the attention control in V4 for specific samples from IT, that is the stressing of the "what" question, as described further on in this document.

The seventh term on the right hand side of equation (10), $I_0$, describes a diffuse spontaneous background entry. A typical value for $I_0$ is 0.025. v stands for stochastic noise of the activity. It is assumed to be the same strength for all pools. A typical average value for v is zero for a Gaussian distribution with a standard deviation of 0.01.

The third term on the right hand side of the equation (10), $$bF(I_k^{V4,l}),$$

describes, as mentioned above, of the inhibitory effect of the inhibitory pool 22 for area V4. The following text refers to FIG. 4. The pools 24 within an area are in competition with each other, a fact which is communicated by an inhibitory pool 22 which receives the excitatory input 27 of all excitatory pools 24 and directs a similar shape restricting of feedback 28 to all excitable pools 24 This inhibiting feedback 28 has a stronger effect on less active pools than on a more active ones. This means that more strongly active pools can win through against less active pools.

Figure 4:
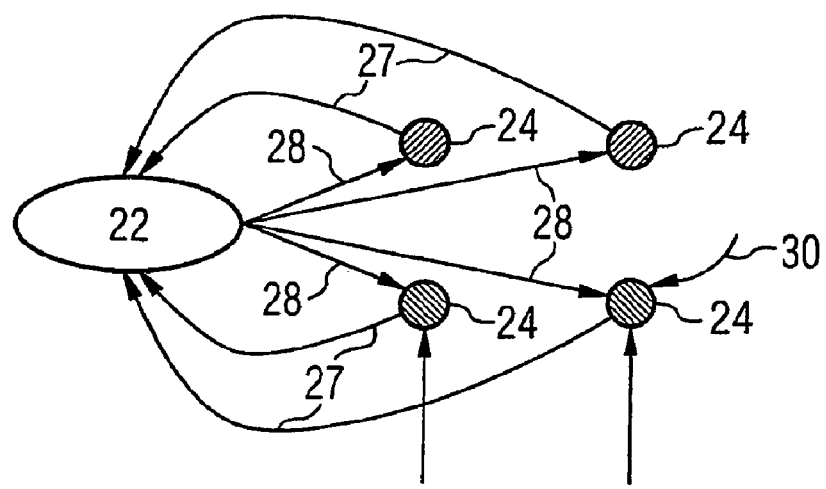
FIG. 4 is a schematic diagram of the interaction between an area and an associated inhibiting pool.

In addition FIG. 4 shows an external input stream 30 (bias) which can excite one or more pools. The precise function of the bias 30 is illustrated further on in this document in connection with equation (15).

The activities $$I_k^{V4,l}$$

within the inhibitory pool satisfy the equation:

$$\tau \frac{\partial}{\partial t} I_k^{V4,l}(t) = -I_k^{V4,l}(t) + c \sum_{pql} F(I_{kpql}^{V4}(t)) - dF(I_k^{V4,l}(t)). \quad (11)$$

The first term on the right hand side of equation (11) again describes the decay of the inhibitory pool 22. The second term describes the input stream V4 in the inhibitory pool 22 belonging to V4 with the index k, scaled through the parameter c. A typical value for c is 0.1.

The third term represents a self-inhibition of the inhibitory pool 22 with the index k belonging to V4. A typical value for d is 0.1.

Experience has shown that the inhibitory effect within V4 only works within a spatial structure of a predefined size, expressed by the octave k. Within the structure of the size k there is competition between the locations P and Q and the orientation l, communicated by the sum $$\sum_{pql} F(I_{kpql}^{V4}(t)).$$

Each index triple (p, q, l) inhibits all other index triples (p, q, l).

Spatial structures of different size k, that is different spatial frequencies k, do not influence each other since the inhibitory effect in equation (10), $$-bF(I_k^{V4,l}),$$

only has a backwards effect on k itself.

The fifth term on the right hand side of equation (10), $$I_{pq}^{V4-PP},$$

describes, as mentioned, the attention control for a feature with the spatial position corresponding to p and q, that is the stressing of the "where" question. the attention control is undertaken by feeding back the activity $$I_{pq}^{V4-PP}$$

of the pools with the indices i and j close to the values p and q from the area PP to all pools with the indices p and q in the area V4. This feedback is modeled by $$I_{pq}^{V4-PP} = \sum_{i=1}^{n} \sum_{j=1}^{n} W_{pqij} F(I_{ij}^{PP}) \qquad (12)$$

where the coefficients $W_{pqij}$ for their part are determined from:

$$W_{pqij} = Ae^{-\frac{dist^2((p,q),(i,j))}{2S^2}} - B \qquad (13)$$

with the coupling constant A (typical value 1.5), with the spatial scaling factor S which defines the extent of the spatial influence of a feature (typically S=2), and with distance function dist(p, q, I, j), which calculates the distance between the location i, j and the midpoint of the Gabor wavelet function defined by p, q. Preferably the Euclidean metric is taken here:

$$dist^2((p,q),(i,j))=(p-i)^2+(q-j)^2. \qquad (14)$$

In addition there is a negative connection B to the environment, which leads to an overstressing of adjacent features and devaluing of more distant features. A typical value for b is 0.01.

In effect the pools with the spatial location corresponding to p and q do not immediately excite the corresponding pools in V4 but only after execution of folding with a Gaussian kernel. in other words: V4 and PP are connected by symmetrical, localized connections which are modeled by the Gaussian weights.

The timing development of the activities $I_{ij}^{PP}$ of the pools in the area PP is specified by $$\tau \frac{\partial}{\partial t} I_{ij}^{PP} = -I_{ij}^{PP} + \tilde{q} F(I_{ij}^{PP}) - bF(I^{PP,I}) + I_{ij}^{PP-V4} + I_{ij}^{PP,A} + I_0 + v. \qquad (15)$$

the equation corresponds in its first, second, sixth and seventh term to the equation (10), but for the area PP.

The third term on the right hand side again describes the inhibitory effect of the common inhibitory pool I for area PP. of which the activity $I_{PP,I}$ satisfies the equation $$\tau \frac{\partial}{\partial t} I^{PP,I} = -I^{PP,I} + c \sum_{i,j} F(I_{ij}^{PP}) - dF(I^{PP,I}). \qquad (16)$$

This equation corresponds in its structure to equation (11) already described. There is only one uniform inhibitory effect for the area PP.

The fourth term on the right hand side of equation (15) again describes the perception controlling feedback of V4 to PP and is specified by $$I_{ij}^{PP-V4} = \sum_{k,p,q,l} W_{pqij} F(I_{kpql}^{V4}), \qquad (17)$$

where the $W_{pqij}$ above was defined in connection with equation (13). the synaptic connections 20 between V4 and PP are also embodied symmetrically. V4 thus controls the attention in PP as regards specific locations ("where" question).

The fifth term $$I_{ij}^{PP,A}$$

on the right hand side of equation (15) is an external top-down bias directing the attention to a specific location (i, j). This is represented in FIG. 4 by the arrow 30. When the bias is preset an object is expected at the preset location. A typical value for this external bias is 0.07 for the expected location and 0 for all other locations.

The sixth term on the right hand side of equation (10), $$I_{kpql}^{V4-IT},$$

describes—as explained—the attention control in V4 for specific patterns from IT, also the stressing of the "what" question. The attention is controlled by feeding back an activity $I_c^{IT}$ of the pools which stand for the pattern c from the area IT to the associated pools in the area V4. This feedback is modeled by $$I_{kpql}^{V4-IT} = \sum_c w_{ckpql} F(I_c^{IT}). \qquad (18)$$

the determination of the weights $w_{ckpql}$ of the input streams of IT into V4 and thereby of the pools belonging to pattern c in area V4 is explained further on in this document.

$I_c^{IT}$ is the activity of a pool which stands for the pattern c in the area IT. the timing development of $I_c^{IT}$ follows the differential equation:

$$\tau \frac{\partial}{\partial t} I_c^{IT} = -I_c^{IT} + \tilde{q} F(I_c^{IT}) - bF(I^{IT,I}) + I_c^{IT-V4} + I_c^{IT,A} + I_c^{IT,A} + \qquad (19)$$
$$I_0 + v.$$

the equation corresponds in its first, second, sixth and seventh terms to equation (10) and (15) and therefore for area IT.

The third term on the right hand side of the equation (19), $-bF(I^{IT,I})$, again describes the inhibitory effect of the inhibitory pool 22 for pattern c of the area IT. The activity $I^{IT,I}$ of the inhibitory pool for the area IT satisfies the equation $$\tau \frac{\partial}{\partial t} I^{IT,I} = -I^{IT,I} + c \sum_c F(I_c^{IT}) - dF(I^{IT,I}). \quad (20)$$

This equation corresponds in its structure to the equations (11) and (16) already described. There is only one uniform inhibitory effect for the area IT which causes the competition for the attention between the individual patterns c.

The fourth term on the right hand side of equation (19), $$I_c^{IT-F4},$$

again describes the attention controlling feedback from V4 to IT and is specified by $$I_c^{IT-V4} = \sum_{k,p,q,l} w_{ckpql} F(I_{kpql}^{V4}), \quad (21)$$

where the $w_{ckpql}$ already occurred in equation (18) and are explained in more detail below. the synaptic connections 20 between V4 and IT are thus embodied symmetrically. V4 thus controls the attention in IT as regards specific patterns ("what" question).

The fifth term on the right hand side of equation (19), $$I_c^{IT,A}$$

is again an external top-down bias directing the attention to a specific pattern c. If the bias is preset a specific pattern c or object c is expected. A typical value for this external bias is 0.07 for the expected pattern and 0 for all other patterns.

The weights $w_{ckpql}$ of the synaptic connections between V4 and IT are embodied by Hebbian Training (Deco, G. and Obradovic, D.: "An information-theoretic Approach to Neurocomputing", Springer Verlag (1996)) with known objects. Expressed in simple terms patterns c are presented to the neuronal network in turn and the weights $w_{ckpql}$ varied until the grandmother pools c in IT recognize the pattern c in each case, i.e. show maximum activity. In a first approximation the following weights are produced $w_{ckpql}$ by the Gabor-Wavelet-transformation of the pattern c stored in IT.

After the training simulations can be conducted with the neural network in order to evaluate an fMRI image for example. The evaluation of an fMRI image basically involves an inverse problem: the cause is to be deduced from the effect (of the activity of certain areas). Because of the complexity of the networking the cause cannot be obtained deductively from the effect. The only possibility is simulation of the effects by variation of a multiplicity of causes.

This is done with the aid of variation of the parameters of the neuronal network depicted, e.g. by switching off individual pools or whole parts of an area. the effect of such assumptions on the neuronal network is calculated by resolving the differential equations specified above and compared with the measured fMRI-images.

The system of the specified differential equations is highly parallel. It consists of around 1.2 million coupled differential equations. These are numerically resolved iteratively, preferably by means of discretization using the Euler or Runge-Kutta method. 1 ms is preferably selected as the timing increment, that is about $T_{refractory}$ as per equation (2).

With the aid of the neuronal network depicted experimental data (Kaster, S.; De Weerd, P.; Desimone, R. and Ungerleider, L.: "Mechanisms of directed attention in the human extrastriate cortex as revealed by functional MRI"; Science 282 (1998) 108-111. Kaster, S.; Pinsk, M.; De Weerd, P.; Desimone, R. and Ungerleider, L.: "Increased activity in human visual cortex during directed attention in the absence of visual stimulation"; Neuron 22 (1999) 751-761.) could be simulated to coordinate. The dynamic of the activity of the pools in V4 with clear changes within one second could be verified. Likewise the attention control by waiting for and the inhibitory effect of simultaneous or related stimuli.

Likewise the medically known phenomenon of "visual neglect" could be illuminated through simulation. "Visual neglect" is the hiding of half of the field of view of the attention or perception although the patient's eyes do not shown any damage. The hiding of the attention is a disturbance in the processing of the accepted visual data by the visual cortex of the brain. In the simulation with the aid of the neurocognitive neuronal network illustrated it was assumed that half of the area PP responsible for localization is damaged. For example one half might exhibit a higher level of noise v. It was possible to show, by resolving the differential equations, that under these circumstances the attention could no longer be directed to this half of the field of view. The pools responsible for this half of the field of view no longer achieved an increased level of activity.

Thus the diagnosis which presents itself for "visual neglect" is damage to the area PP responsible for localization.

Within the framework of the invention numerous variations and developments of the exemplary embodiments described can be implemented. In particular the invention can, if applied to the corresponding suitable areas of the brain, be used for diagnosis of all neuropsychological phenomena, i.e. all disturbances to the correct functioning of the brain.

Although other modifications and changes may be suggested by those skilled in the art, it is the intention of the inventors to embody within the patent warranted hereon all changes and modifications as reasonably and properly come within the scope of their contribution to the art.

The invention claimed is:

1. A method for evaluating an image of the brain in a form of an fMRI image obtained by functional magnetic resonance tomography, comprising the steps of:
   a) using a neuronal network to simulate activities of the brain;
   b) simulating a disturbance suspected in the brain in the neuronal network by providing a disturbed neuronal network;
   c) comparing activity determined in the disturbed neuronal network with activity of the brain observed in the fMRI image; and
   d) from said comparing step creating a finding which provides assumed conclusions about disturbances in the brain, providing said finding to medical personnel as support for a diagnosis.

2. A method in accordance with claim 1, wherein the neuronal network used for simulation of the activity of the brain simulates the activity of the neurons in such a way that a majority of the neurons of the neuronal network are assembled into a plurality of pools; and further comprising the step of:
   simulating activity of the pools.

3. A method in accordance with claim 1, wherein the neuronal network used for simulation of the activity of the brain simulates the activity of the brain in such a way that the activity of the brain occurs in functionally differentiated areas.

4. A method in accordance with claim 2, further comprising the step of:
   selecting areas so that they each feature a plurality of pools.

5. A method according to claim 2, wherein said pools are in competition with each other for attention; and further comprising the step of:
   communicating said competition via at least one inhibitory pool which exercises an inhibitory effect on activity of the pools.

6. A method in accordance with claim 1, further comprising the steps of:
   analyzing activity of the brain during a seeing process; and
   using a wavelet transformation in the neuronal network to analyze a recorded image of the brain activity.

7. A method according to claim 4, further comprising the steps of:
   analyzing activity of the brain during a seeing process; and
   identifying an area of the neuronal network that has a function of identifying objects within a field of vision, said pools of said area being specialized in identifying specific objects in each case.

8. A method according to claim 7, further comprising the steps of:
   analyzing the activity of the brain during a seeing process; and
   identifying an area of the neuronal network that has a function of identifying a location of a detectable object in a field of vision, said pools of said area being specialized in localization of objects at specific locations in the field of vision.

9. A method according to claim 7, wherein the neuronal network is designed so that attention is increased for a specific object to be identified or for a specific object to be localized.

10. An arrangement for evaluating an image of a brain in a form of an fMRI image obtained by functional magnetic resonance tomography, comprising:
    a) a neuronal network trained to simulate activity of the brain;
    b) means for simulating a suspected disturbance in the brain in the neuronal network to provide a disturbed neuronal network;
    c) means for comparison of activity determined in the disturbed neuronal network with activity of the brain observed in the fMRI image; and
    d) means for creating a finding from the comparison which provides assumed conclusions about disturbances in the brain, said finding providing support for a diagnosis.

11. A device for evaluating an image of the brain as an fMRI image obtained by functional magnetic resonance tomography, comprising:
    a) means for creating an fMRI image of the brain of a patient; and
    b) an arrangement for evaluating the fMRI including
    c) a neuronal network used to simulate the activity of the brain;
    d) means for simulating a suspected disturbance in the brain in the neuronal network (disturbed neuronal network);
    e) means for comparison of the activity determined in the disturbed neuronal network with the activity of the brain observed in the fMRI image; and
    f) means for creating a finding from the comparison which provides assumed conclusions about disturbances in the brain, said finding providing support for a diagnosis.

12. A computer readable medium including a computer program for evaluating an image for a brain in a form of an fMRI image obtained by functional magnetic resonance tomography, comprising:
    software code executable on a computer to:
        provide a neuronal network trained to simulate activity of the brain;
        simulate a disturbance suspected in the brain in the neuronal network by providing a disturbed neuronal network;
        compare activity determined in the disturbed neuronal network with activity of the brain observed in fMRI image; and
        create a finding from the comparison that provides assumed conclusions about disturbance in the said finding providing support for a diagnosis brain.

* * * * *

UNITED STATES PATENT AND TRADEMARK OFFICE
CERTIFICATE OF CORRECTION

PATENT NO. : 7,349,728 B2  Page 1 of 1
APPLICATION NO. : 10/499619
DATED : March 25, 2008
INVENTOR(S) : Silvia Corchs et al.

It is certified that error appears in the above-identified patent and that said Letters Patent is hereby corrected as shown below:

On the Title page of the patent, Item (22) please correct the incorrect PCT Filed date of Sep. 12, 2002 to the correct filing date as follows:

PCT Filed: December 9, 2002

Signed and Sealed this

Fourth Day of August, 2009

JOHN DOLL
*Acting Director of the United States Patent and Trademark Office*